(12) United States Patent
Hercouet et al.

(10) Patent No.: US 7,988,738 B2
(45) Date of Patent: Aug. 2, 2011

(54) PROCESS FOR THE LIGHTENING DYEING OF KERATIN MATERIALS USING AN EMULSION COMPRISING A DYE AND AN ALKALINE AGENT AND AN OXIDIZING COMPOSITION

(75) Inventors: Leïla Hercouet, Neuilly Plaisance (FR); Anne-Laure Bernard, Antony (FR); Dominique Bordeaux, Soisy sur Seine (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 12/642,506

(22) Filed: Dec. 18, 2009

(65) Prior Publication Data

US 2010/0154141 A1 Jun. 24, 2010

Related U.S. Application Data

(60) Provisional application No. 61/150,445, filed on Feb. 6, 2009.

(30) Foreign Application Priority Data

Dec. 19, 2008 (FR) ..................................... 08 07322

(51) Int. Cl.
*A61Q 5/10* (2006.01)
(52) U.S. Cl. ............ 8/405; 8/406; 8/410; 8/421; 8/435; 8/620; 132/202; 132/208
(58) Field of Classification Search .............. 8/405, 406, 8/410, 421, 435, 620; 132/202, 208
See application file for complete search history.

(56) References Cited

U.S. PATENT DOCUMENTS

| | | | |
|---|---|---|---|
| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,826,681 A | 5/1989 | Jacquet et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |

(Continued)

FOREIGN PATENT DOCUMENTS

CA 1 268 421 5/1990

(Continued)

OTHER PUBLICATIONS

French Search Report for FR 0807322, dated Sep. 24, 2009.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.

(Continued)

*Primary Examiner* — Eisa B Elhilo
(74) *Attorney, Agent, or Firm* — Finnegan, Henderson, Farabow, Garrett & Dunner, LLP

(57) ABSTRACT

Provided herein is a process for dyeing keratin materials, comprising: applying to said keratin materials a dyeing composition, comprising, a direct emulsion (A) comprising at least one fatty substance other than fatty acids present in an amount greater than 25% by weight; at least one surfactant; at least one alkaline agent; at least one colored or coloring entity chosen from direct dyes and oxidation dyes; and water in an amount greater than 5% by weight relative to the total weight of the direct emulsion (A); and a composition (B) comprising at least one oxidizing agent. Also provided herein is a multi-compartment device comprising, in a first compartment, a direct emulsion (A) comprising at least one fatty substance other than fatty acids present in an amount greater than 25% by weight; at least one surfactant; at least one alkaline agent; at least one colored or coloring entity chosen from direct dyes and oxidation dyes; and water in an amount greater than 5% by weight relative to the total weight of the direct emulsion (A); and, in another compartment, a composition (B) comprising at least one oxidizing agent.

22 Claims, No Drawings

U.S. PATENT DOCUMENTS

| | | |
|---|---|---|
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,740,663 B2 | 6/2010 | De La Mettrie et al. |
| 7,766,977 B2 | 8/2010 | Cottard et al. |
| 7,799,095 B2 | 9/2010 | Mario et al. |
| 2003/0190297 A1 | 10/2003 | Narasimhan et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2004/0235700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1* | 4/2006 | Chan et al. ............ 8/405 |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1* | 11/2006 | Legrand ............ 8/405 |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 A1 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 B1 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 449 512 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |

| | | |
|---|---|---|
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 A2 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
Copending U.S. Appl. No. 12/976,093, filed Dec. 22, 2010.
Copending U.S. Appl. No. 12/976,124, filed Dec. 22, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 023 891, dated Aug. 2, 2000.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 716 840, dated Nov. 2, 2006.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 892 623, dated May 4, 2007.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French. Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.

French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
French Search Report for FR 09/59388, dated Aug. 3, 2010.
French Search Report for FR 09/59391, dated Sep. 16, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl. No. 12/642,473.
Notice of Allowance mailed in co-pending U.S. Appl. No. 12/339,753, dated Jul. 9, 2010.
Notice of Allowance mailed Jan. 28, 2011, in U.S. Appl. No. 12/642,592.
Notice of Allowance mailed Jun. 11, 2010, in U.S. Appl. No. 12/642,489.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
INotice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Dec. 17, 2010, in co-pending U.S. Appl. No. 12/642,451.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Nov. 22, 2010, in co-pending U.S. Appl. No. 12/642,593.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

PROCESS FOR THE LIGHTENING DYEING OF KERATIN MATERIALS USING AN EMULSION COMPRISING A DYE AND AN ALKALINE AGENT AND AN OXIDIZING COMPOSITION

This application claims benefit of U.S. Provisional Application No. 61/150,445, filed Feb. 6, 2009. This application also claims benefit of priority under 35 U.S.C. §119 to French Patent Application No. 0807322, filed Dec. 19, 2008.

Provided herein is a process for the lightening dyeing of human keratin materials, for example the hair.

Processes for lightening human keratin materials such as keratin fibers may generally use an aqueous composition comprising at least one oxidizing agent, often under alkaline pH conditions. The oxidizing agent has the role of degrading the melanin of the hair, which, depending on the nature of the oxidizing agent present, can lead to a more or less pronounced lightening of the fibers. Thus, for relatively weak lightening, the oxidizing agent may generally be hydrogen peroxide. When greater lightening is sought, peroxygenated salts may often be used, for instance persulfates, in the presence of hydrogen peroxide.

One of the difficulties that may arise from a lightening process occurs when the process is performed under alkaline conditions and the alkaline agent most commonly used is aqueous ammonia. Aqueous ammonia may be frequently used in processes of this type since it allows the pH of the composition to be adjusted to an alkaline pH to enable degradation of the oxidizing agent. Moreover, aqueous ammonia may also cause swelling of the keratin fiber, with opening of the scales, which may promote the penetration of the oxidizing agent into the fiber, and thus increase the efficacy of the reaction.

However, aqueous ammonia may be very volatile, which users may find disagreeable due to the characteristic strong, rather unpleasant odor of ammonia that may be given off during the process.

Furthermore, the amount of ammonia given off may necessitate the use of higher amounts in order to compensate for this loss. This may affect the user, who not only remains inconvenienced by the odor, but may also be confronted with greater risks of intolerance, for instance irritation of the scalp (stinging).

Replacing all or some of the aqueous ammonia with at least one other standard basifying agent may not lead to compositions that are as efficient as those based on aqueous ammonia since these basifying agents may not afford sufficient lightening of pigmented fibers in the presence of the oxidizing agent.

In the context of dyeing the hair, at least one oxidizing composition may be used for permanently dyeing the hair starting with dye precursors such as oxidation bases and couplers. In the context of direct dyeing, although this method may not involve the use of an oxidizing agent to develop the coloration, at least one oxidizing agent may be used to obtain a lightening effect with the dyeing. This is then referred to as direct dyeing or semi-permanent dyeing under lightening conditions.

The at least one oxidizing agent has the role of degrading the melanin of the hair, which, depending on the nature of the oxidizing agent present, may lead to more or less pronounced lightening of the fibers. Thus, for relatively weak lightening, the oxidizing agent may generally be hydrogen peroxide. When greater lightening is sought, peroxygenated salts may be used, for instance persulfates, in the presence of hydrogen peroxide.

One of the difficulties that may arise occurs when these processes are performed under alkaline conditions and the alkaline agent most commonly used is aqueous ammonia. The use of aqueous ammonia may be beneficial in processes of this type since it allows the pH of the composition to be adjusted to an alkaline pH to enable activation of the oxidizing agent. However, aqueous ammonia may also cause swelling of the keratin fiber, with opening of the scales, which may promote the penetration of the oxidizing agent, and also of the dyes, for example the oxidation dyes, into the fiber, and thus increase the efficacy of the dyeing reaction.

However, aqueous ammonia may be very volatile, which users may find disagreeable due to the characteristic strong, rather unpleasant odor of ammonia that may be given off during the process.

Furthermore, the amount of ammonia given off may necessitate the use of higher amounts in order to compensate for this loss. This may affect the user, who not only remains inconvenienced by the odor, but may also be confronted with greater risks of intolerance, for instance irritation of the scalp, which is reflected especially by stinging.

Replacing all or some of the aqueous ammonia with at least one other standard basifying agent may not lead to compositions that are as efficient as those based on aqueous ammonia since these basifying agents may not afford sufficient lightening of pigmented fibers in the presence of the oxidizing agent.

Thus, the subject matter of the present disclosure, inter alia, may in some embodiments be performed in the presence of at least one oxidizing agent, which may not have the drawbacks of the existing processes, while at the same time may remain at least as effective, in both the strength of the coloration obtained and the chromaticity and the uniformity of coloration obtained along the fiber.

Provided herein is a process for dyeing keratin materials, comprising:
  applying to said keratin materials a dyeing composition comprising,
  a direct emulsion (A) comprising at least one fatty substance other than fatty acids present in an amount greater than 25% by weight, for example in an amount greater than 50% by weight; at least one surfactant; at least one alkaline agent; at least one colored or coloring entity chosen from direct dyes and oxidation dyes; and water in an amount greater than 5% by weight relative to the total weight of the direct emulsion (A); and
  a composition (B) comprising at least one oxidizing agent.

Also provided is a multi-compartment device comprising, in a first compartment, a direct emulsion (A) comprising at least one fatty substance other than fatty acids present in an amount greater than 25% by weight; at least one surfactant; at least one alkaline agent; at least one colored or coloring entity chosen from direct dyes and oxidation dyes; and water in an amount greater than 5% by weight relative to the total weight of the direct emulsion, and, in another compartment, a composition (B) comprising at least one oxidizing agent.

As described herein, a direct emulsion is an oil-in-water emulsion.

Hereinafter, unless otherwise indicated, the limits of a range of values are included in that range.

The keratin materials treated by the process described herein may be, for example, bodily hair, eyelashes, and head hair. The process described herein may obtain a good level of lightening of the keratin materials, such as head hair, without giving off an odor of ammonia, which may be an irritant.

In some embodiments, the direct emulsion (A) may for example contain water in an amount less than 50% by weight relative to the total weight of the direct emulsion (A), for instance in an amount ranging from 10% to 50% by weight.

In some embodiments, the oil-in-water emulsion described herein may comprise at least one fatty substance.

"Fatty substance" means, as used herein, an organic compound that is insoluble in water at room temperature (25° C.) and at atmospheric pressure (760 mm Hg) and is soluble in an amount less than 5% by weight, for example 1% and for instance 0.1%. In some embodiments, the fatty substance may contain in its structure a sequence of at least two siloxane groups or at least one hydrocarbon-based chain containing at least 6 carbon atoms. In certain embodiments, the fatty substance may be soluble in organic solvents at 25° C. and at atmospheric pressure (760 mm Hg), for instance chloroform, ethanol, benzene, or decamethylcyclopentasiloxane.

According to the disclosure, the direct emulsion (A) comprises at least one fatty substance other than fatty acids present in an amount greater than 25% by weight.

The at least one fatty substance may be chosen for example from lower alkanes, fatty alcohols, fatty acid esters, fatty alcohol esters, oils, for example non-silicone mineral, plant, animal, or synthetic oils, non-silicone waxes, and silicones.

It is recalled that, for the purposes of the disclosure, the fatty alcohols and fatty esters for example contain at least one linear or branched, saturated or unsaturated hydrocarbon-based group containing 6 to 30 carbon atoms, which may be optionally substituted with for example at least one hydroxyl group, and for instance 1 to 4 hydroxyl groups. In certain embodiments, the fatty alcohols and fatty esters may be unsaturated, containing one to three conjugated or non-conjugated carbon-carbon double bonds.

In some embodiments, the lower alkanes may for example comprise from 6 to 16 carbon atoms and are linear or branched, and optionally cyclic. By way of a non-limiting example, the lower alkanes may be chosen from hexane and dodecane, and isoparaffins, for instance isohexadecane and isodecane.

As examples of oils that may be used in the composition described herein, non-limiting mention may be made of:

hydrocarbon-based oils of animal origin, such as perhydrosqualene;

hydrocarbon-based oils of plant origin, such as liquid fatty acid triglycerides containing from 6 to 30 carbon atoms, for instance heptanoic or octanoic acid triglycerides, or, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons of mineral or synthetic origin, of more than 16 carbon atoms, liquid paraffins, petroleum jelly, liquid petroleum jelly, polydecenes, and hydrogenated polyisobutene such as PARLEAM®;

fluoro oils, for instance perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; per-fluoromorpholine derivatives such as 4-trifluoromethyl perfluoromorpholine sold under the name PF 5052® by the company 3M.

In some embodiments, the fatty alcohols may be non-oxyalkylenated. They may be saturated or unsaturated, linear or branched, and contain 6 to 30 carbon atoms, for example from 8 to 30 carbon atoms; non-limiting mention may be made of cetyl alcohol, stearyl alcohol and a mixture thereof (cetylstearyl alcohol), octyldodecanol, 2-butyloctanol, 2-hexyldecanol, 2-undecylpentadecanol, oleyl alcohol, and linoleyl alcohol.

In some embodiments, the waxes may be chosen from carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used include for example marine waxes such as the product sold by the company Sophim under the reference M82, and polyethylene waxes or polyolefin waxes.

In some embodiments, the esters may be esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, wherein the total carbon number of the esters may be greater than or equal to 10.

Among the monoesters, non-limiting mention may be made of: dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, and 2-hexyldecyl laurate.

In some embodiments, esters of $C_4$-$C_{22}$ dicarboxylic or tricarboxylic acids, of $C_1$-$C_{22}$ alcohols and esters of mono-, di- or tricarboxylic acids, and of $C_2$-$C_{26}$ di-, tri-, tetra- or pentahydroxy alcohols may also be used.

Non-limiting mention may for example be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters described herein, non-limiting mention may be made of: ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate, and cetyl octanoate.

In some embodiments, the composition described herein may also comprise, as fatty esters, sugar esters and diesters of $C_6$-$C_{30}$, for example $C_{12}$-$C_{22}$ fatty acids. "Sugar" means, as used herein, oxygen-bearing hydrocarbon-based derivatives containing several alcohol functions, with or without aldehyde or ketone functions, and which contain at least 4 carbon atoms. The sugars may be monosaccharides, oligosaccharides, or polysaccharides.

As examples of sugars, non-limiting mention may be made of: sucrose (or saccharose), glucose, galactose, ribose, fucose, maltose, fructose, mannose, arabinose, xylose and lactose, and derivatives thereof, for example alkyl derivatives, such as methyl derivatives, for instance methylglucose.

In some embodiments, the sugar esters of fatty acids may be chosen for example from the group comprising the esters or mixtures of esters of sugars described herein and of linear or branched, saturated or unsaturated $C_6$-$C_{30}$ and for example $C_{12}$-$C_{22}$ fatty acids. In some embodiments, the sugar esters of fatty acids may be unsaturated and may comprise one to three conjugated or nonconjugated carbon-carbon double bonds.

In certain embodiments, the esters may also be chosen from mono-, di-, tri-, tetraesters and polyesters, and mixtures thereof.

In some embodiments, the esters may be chosen, for example, from oleates, laurates, palmitates, myristates, behenates, cocoates, stearates, linoleates, linolenates, caprates and arachidonates, or mixtures thereof such as, for example, oleo-palmitate, oleo-stearate and palmito-stearate mixed esters.

In some embodiments, monoesters and diesters, for example sucrose, glucose or methylglucose mono- or dioleates, stearates, behenates, oleopalmitates, linoleates, linolenates and oleostearates may be used.

As an example, non-limiting mention may be made of the product sold under the name GLUCATE® DO by the company Amerchol, which is a methylglucose dioleate.

As examples of esters or mixtures of esters of sugar and of fatty acid non-limiting mention may for example be made of:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed from 20% monoester and 80% di-tri-ester-polyester; and
the sucrose mono-dipalmito-stearate sold by the company Goldschmidt under the name TEGOSOFT® PSE.

In some embodiments, the silicones that may be used in the cosmetic compositions described herein are volatile or non-volatile, cyclic, linear or branched silicones, which may be unmodified or modified with organic groups, having a viscosity from $5 \times 10^{-6}$ to $2.5$ m$^2$/s at 25° C., and for example $1 \times 10^{-6}$ to $1$ m$^2$/s.

In some embodiments, the silicones that may be used may be in the form of oils, waxes, resins, or gums.

In some embodiments, for example, the silicone may be chosen from polydialkylsiloxanes, such as polydimethylsiloxanes (PDMS), and organomodified polysiloxanes comprising at least one functional group chosen from poly(oxyalkylene) groups, amino groups, and alkoxy groups.

Organopolysiloxanes are defined in greater detail in Walter Noll's "Chemistry and Technology of Silicones" (1968) Academic Press. They may be volatile or non-volatile.

In some embodiments, when they are volatile, the silicones may for example be chosen from those having a boiling point ranging from 60° C. to 260° C., and for example from:
(i) cyclic polydialkylsiloxanes containing from 3 to 7 silicon atoms, for example 4 to 5 silicon atoms. These may be, for example, octamethylcyclotetrasiloxane sold for instance under the name VOLATILE SILICONE® 7207 by Union Carbide or SILBIONE® 70045 V 2 by Rhodia, decamethylcyclopentasiloxane sold under the name VOLATILE SILICONE® 7158 by Union Carbide, and SILBIONE® 70045 V 5 by Rhodia, and mixtures thereof.

Non-limiting mention may also be made of cyclocopolymers of the dimethylsiloxane/methylalkylsiloxane type, such as VOLATILE SILICONE® FZ 3109 sold by the company Union Carbide, of formula:

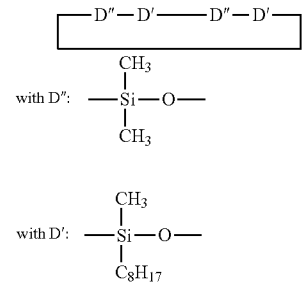

Non-limiting mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;
(ii) linear volatile polydialkylsiloxanes containing 2 to 9 silicon atoms and having a viscosity of less than or equal to $5 \times 10^{-6}$ m$^2$/s at 25° C. An example may be decamethyltetrasiloxane sold for example under the name SH 200 by the company Toray Silicone. Silicones belonging to this category may also be described in the article published in Cosmetics and Toiletries, Vol. 91, January 76, pp. 27-32, Todd & Byers "Volatile Silicone Fluids for Cosmetics".

In some embodiments, non-volatile polydialkylsiloxanes, polydialkylsiloxane gums and resins, polyorganosiloxanes modified with organofunctional groups above, and mixtures thereof, may for example be used.

In some embodiments, the silicones may for example be chosen from polydialkylsiloxanes, among which non-limiting mention may be made of polydimethylsiloxanes containing trimethylsilyl end groups. The viscosity of the silicones is measured, for example, at 25° C. according to ASTM standard 445 Appendix C.

Among the polydialkylsiloxanes, non-limiting mention may be made of the following commercial products:
the SILBIONE® oils of the 47 and 70 047 series or the MIRASIL® oils sold by Rhodia, for instance the oil 70 047 V 500 000;
the oils of the MIRASIL® series sold by the company Rhodia;

the oils of the 200 series from the company Dow Corning, such as DC200 with a viscosity of 60,000 mm²/s;

the VISCASIL® oils from General Electric and certain oils of the SF series (SF 96, SF 18) from General Electric.

Non-limiting mention may also be made of polydimethylsiloxanes containing dimethylsilanol end groups known under the name Dimethiconol (CTFA), such as the oils of the 48 series from the company Rhodia.

As examples of polydialkylsiloxanes, non-limiting mention may also be made of the products sold under the names ABIL WAX® 9800 and 9801 by the company Goldschmidt, which are poly($C_1$-$C_{20}$)dialkylsiloxanes.

In some embodiments, the silicone gums that can be used are for example polydialkylsiloxanes such as polydimethylsiloxanes with high number-average molecular masses of between 200,000 and 1,000,000, used alone or as a mixture in a solvent. The solvent can be chosen from volatile silicones, polydimethylsiloxane (PDMS) oils, polyphenylmethylsiloxane (PDMS) oils, isoparaffins, polyisobutylenes, methylene chloride, pentane, dodecane and tridecane, or mixtures thereof.

In some embodiments, products that can be used are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane;

mixtures of two PDMSs with different viscosities, for example a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of $5 \times 10^{-6}$ m²/s. This product for example contains 15% SE 30 gum and 85% SF 96 oil.

In some embodiments, the organopolysiloxane resins that can be used are crosslinked siloxane systems containing the following units:

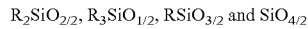

wherein R is a hydrocarbon-based group containing 1 to 16 carbon atoms. In some embodiments, R is a $C_1$-$C_4$ lower alkyl radical, for example methyl.

In some embodiments, as examples of resins, non-limiting mention may be made of the product sold under the name Dow Corning 593 or those sold under the names Silicone Fluid SS 4230 and SS 4267 by the company General Electric, which are silicones of dimethyl/trimethyl siloxane structure.

Non-limiting mention may also be made of trimethyl siloxysilicate type resins sold in particular under the names X22-4914, X21-5034 and X21-5037 by the company Shin-Etsu.

In some embodiments, the organomodified silicones that can be used may be silicones described herein and comprising at least one organofunctional group attached via a hydrocarbon-based group.

Besides the silicones described herein, the organomodified silicones may be polydiarylsiloxanes, for example polydiphenylsiloxanes, and polyalkylarylsiloxanes functionalized with the organofunctional groups described herein.

The polyalkylarylsiloxanes may be chosen for example from linear and/or branched polydimethyl/methylphenylsiloxanes and polydimethyl/diphenylsiloxanes with a viscosity of from $1 \times 10^{-5}$ to $5 \times 10^{-2}$ m²/s at 25° C.

In some embodiments, as examples of the polyalkylarylsiloxanes, non-limiting mention may be made of the products sold under the following names:

the SILBIONE® oils of the 70 641 series from Rhodia;

the oils of the RHODORSIL® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, non-limiting mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. In some embodiments, the substituted amine groups may be, for example, $C_1$-$C_4$ aminoalkyl groups;

alkoxylated groups such as the product sold under the name Silicone Copolymer F-755 by SWS Silicones, and ABIL WAX® 2428, 2434 and 2440 by the company Goldschmidt.

In some embodiments, the at least one fatty substance may be neither oxyalkylenated nor glycerolated.

For example, the at least one fatty substance other than fatty acids may be chosen from compounds that are liquid or pasty at room temperature and at atmospheric pressure.

In some embodiments, the at least one fatty substance may be a compound that is liquid at a temperature of 25° C. and at atmospheric pressure.

In some embodiments, the at least one fatty substance may for example be chosen from $C_6$-$C_{16}$ lower alkanes, fatty alcohols, fatty acid esters, fatty alcohol esters, nonsilicone oils of animal origin containing more than 16 carbon atoms or of plant or synthetic origin, and silicones.

In some embodiments, the at least one fatty substance may be chosen from liquid petroleum jelly, polybutenes, liquid esters of fatty acids or of fatty alcohols, or mixtures thereof. In certain embodiments, the at least one fatty substance may be non-silicone.

In some embodiments, alkanes or hydrocarbons and silicones may for example be chosen.

The direct emulsion (A) described herein may comprise at least one fatty substance present in an amount greater than 25% by weight relative to the total weight of the direct emulsion (A). In some embodiments, the at least one fatty substance may be present in an amount ranging from 25% to 80% by weight relative to the total weight of the direct emulsion (A), for example from 25% to 65% by weight and for instance from 30% to 55%.

In some embodiments, the direct emulsion (A) may further comprise at least one surfactant.

In certain embodiments, the at least one surfactant may be chosen from nonionic surfactants or from anionic surfactants, for example nonionic surfactants.

In some embodiments, the anionic surfactants may be chosen, for example, from the salts (for example, alkali metal salts, such as sodium salts, ammonium salts, amine salts, amino alcohol salts, or alkaline-earth metal salts such as magnesium salts) of the following anionic surfactants:

alkyl sulfates, alkyl ether sulfates, alkylamido ether sulfates, alkylaryl polyether sulfates, monoglyceride sulfates;

alkylsulfonates, alkylamidesulfonates, alkylarylsulfonates, α-olefin sulfonates, paraffin sulfonates;

alkyl phosphates, alkyl ether phosphates;

alkylsulfosuccinates, alkyl ether sulfosuccinates, alkylamidesulfosuccinates; alkylsulfosuccinates;

alkylsulfoacetates;

acylsarcosinates; acylisethionates and N-acyltaurates;

salts of fatty acids such as oleic acid, ricinoleic acid, palmitic acid or stearic acid, coconut oil acid, or hydrogenated coconut oil acid;

alkyl-D-galactoside uronic acid salts;

acyllactylates;

salts of polyoxyalkylenated alkyl ether carboxylic acids, of polyoxyalkylenated alkylaryl ether carboxylic acids, or of polyoxyalkylenated alkylamido ether carboxylic acids, for example those containing from 2 to 50 ethylene oxide groups;

and mixtures thereof.

In some embodiments, the alkyl or acyl radical of the surfactants may contain from 6 to 24 carbon atoms, for example from 8 to 22 carbon atoms and for instance from 18 to 22 carbon atoms, and the aryl radical may for example contain a phenyl or benzyl group.

In some embodiments, the nonionic surfactants may for example be chosen from monooxyalkylenated, polyoxyalkylenated, monoglycerolated, and polyglycerolated nonionic surfactants. The oxyalkylene units can for example be oxyethylene or oxypropylene units, or a combination thereof, for example oxyethylene units.

Non-limiting examples of oxyalkylenated nonionic surfactants that may be mentioned include:

oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyethylenated esters of saturated or unsaturated, linear or branched, $C_8$-$C_{30}$ acids and of sorbitol, saturated or unsaturated, oxyethylenated plant oils, condensates of ethylene oxide and/or of propylene oxide, inter alia, alone or as mixtures.

In some embodiments, the at least one surfactant may contain a number of moles of ethylene oxide and/or of propylene oxide ranging from 1 to 100, for example from 2 to 50. In certain embodiments, the nonionic surfactants may not comprise any oxypropylene units.

In some embodiments, the oxyalkylenated nonionic surfactants may be chosen from oxyethylenated $C_8$-$C_{30}$ alcohols and for example oxyethylenated $C_{18}$-$C_{30}$ amines.

Non-limiting examples of ethoxylated fatty alcohols that may be mentioned include the adducts of ethylene oxide with lauryl alcohol, for example those containing from 9 to 50 oxyethylene groups and for instance those containing from 10 to 12 oxyethylene groups (Laureth-10 to Laureth-12, as the CTFA names); the adducts of ethylene oxide with behenyl alcohol, for example those containing from 9 to 50 oxyethylene groups (Beheneth-9 to Beheneth-50, as the CTFA names); the adducts of ethylene oxide with cetearyl alcohol (mixture of cetyl alcohol and stearyl alcohol), for example those containing from 10 to 30 oxyethylene groups (Ceteareth-10 to Ceteareth-30, as the CTFA names); the adducts of ethylene oxide with cetyl alcohol, for example those containing from 10 to 30 oxyethylene groups (Ceteth-10 to Ceteth-30, as the CTFA names); the adducts of ethylene oxide with stearyl alcohol, for example those containing from 10 to 30 oxyethylene groups (Steareth-10 to Steareth-30, as the CTFA names); the adducts of ethylene oxide with isostearyl alcohol, for example those containing from 10 to 50 oxyethylene groups (Isosteareth-10 to Isosteareth-50, as the CTFA names); and mixtures thereof.

Non-limiting examples of ethoxylated fatty acids that may be mentioned include the adducts of ethylene oxide with lauric acid, palmitic acid, stearic acid, or behenic acid, and mixtures thereof, for example those containing from 9 to 50 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); and mixtures thereof.

Mixtures of the oxyethylenated derivatives of fatty alcohols and of fatty acids may also be used.

In some embodiments, the direct emulsion (A) comprises at least one ethoxylated fatty alcohol, for example at least behenyl alcohol.

As non-limiting examples of monoglycerolated or polyglycerolated nonionic surfactants, monoglycerolated or polyglycerolated $C_8$-$C_{40}$ alcohols may for example be used.

In some embodiments, the monoglycerolated or polyglycerolated $C_8$-$C_{40}$ alcohols have the following formula:

wherein R is a linear or branched $C_8$-$C_{40}$ alkyl or alkenyl radical, for example $C_8$-$C_{30}$, and m is a number ranging from 1 to 30, for example from 1 to 10.

As examples of alcohols, non-limiting mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols so that the value of m is a statistical value, which means that, in a commercial product, several species of polyglycerolated fatty alcohol may coexist in the form of a mixture.

Among the monoglycerolated or polyglycerolated alcohols, the C8/C10 alcohol containing 1 mol of glycerol, the C10/C12 alcohol containing 1 mol of glycerol and the C12 alcohol containing 1.5 mol of glycerol may for example be used.

In some embodiments, the at least one surfactant present in the direct emulsion (A) is a nonionic surfactant with an HLB value ranging from 8 to 18. The HLB is the ratio between the hydrophilic part and the lipophilic part in the molecule. The term "HLB" is well known to those skilled in the art and is described in "The HLB system. A time-saving guide to emulsifier selection" (published by ICI Americas Inc., 1984).

In some embodiments, the at least one surfactant may be chosen from nonionic surfactants.

The at least one surfactant in the direct emulsion (A) can be present in an amount ranging for example from 0.1% to 50% by weight and for instance from 0.5% to 30% by weight relative to the total weight of the direct emulsion (A).

The direct emulsion (A) may be prepared via standard processes of direct emulsion preparation, but also via a phase inversion temperature (or PIT) process. The principle of emulsification via PIT is, in its principle, known to those skilled in the art; it was described in 1968 by K. Shinoda (J. Chem. Soc. Jpn., 1968, 89, 435). The PIT emulsification technique has been used to obtain stable fine emulsions (K. Shinoda and H. Saito, J. Colloid Interface Sci., 1969, 30, 258). The PIT emulsification technique has been applied in cosmetics as early as 1972 by Mitsui et al. ("Application of the phase-inversion-temperature method to the emulsification of cosmetics"; T. Mitsui, Y. Machida and F. Harusawa, American Cosmet. Perfum., 1972, 87, 33).

The principle of the PIT technique is as follows: a mixture of an aqueous phase and an oily phase may be prepared and may be brought to a temperature above the PIT temperature, the phase inversion temperature of the system, which is the temperature at which the equilibrium between the hydrophilic and lipophilic properties of the at least one emulsifier used is reached; at elevated temperature, i.e. above the phase inversion temperature (>PIT), the emulsion is of a water-in-oil type, and, during its cooling, the emulsion inverts at the phase inversion temperature, to become an emulsion of an oil-in-water type, and in doing so by passing previously through a state of microemulsion. In some embodiments, the at least one nonionic surfactant has an HLB value ranging from 8 to 18. In certain embodiments, ethoxylated fatty alcohols, ethoxylated fatty acids, ethoxylated fatty acid partial glycerides, and polyglycerolated fatty acid triglycerides, and ethoxylated derivatives thereof, and mixtures thereof may be used. Moreover, in some embodiments, an emulsion may have a particle size of less than 4 microns, for example less than 1 μm.

In some embodiments, the direct emulsion (A) described herein may comprise at least one alkaline agent.

The at least one alkaline agent may be chosen from mineral bases, organic amines and organic amine salts, alone or as a mixture.

Non-limiting examples of organic amines that may be mentioned include organic amines with a pKb value at 25° C. of less than 12, for example less than 10 and for instance less than 6. In some embodiments, the pKb corresponds to the function of highest basicity.

The organic amine may comprise one or two primary, secondary, or tertiary amine functions, and at least one linear or branched $C_1$-$C_8$ alkyl groups bearing at least one hydroxyl radical.

In some embodiments, organic amines may be chosen from alkanolamines such as mono-, di-, or trialkanolamines, comprising one to three identical or different $C_1$-$C_4$ hydroxyalkyl radicals.

Among the organic amines, non-limiting mention may be made of: monoethanolamine, diethanolamine, triethanolamine, monoisopropanolamine, diisopropan-olamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris(hydroxymethylamino)methane.

In some embodiments, organic amines having the following formula:

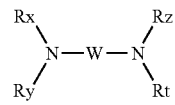

wherein W is a $C_1$-$C_6$ alkylene residue optionally substituted with a hydroxyl group or a $C_1$-$C_6$ alkyl radical; Rx, Ry, Rz and Rt, which may be identical or different, are a hydrogen atom or a $C_1$-$C_6$ alkyl, $C_1$-$C_6$ hydroxyalkyl, or $C_1$-$C_6$ aminoalkyl radical, may for example be used.

Non-limiting examples of organic amines that may be mentioned include 1,3-diaminopropane, 1,3-diamino-2-propanol, spermine, and spermidine.

In some embodiments, the organic amine is chosen from amino acids.

In some embodiments, the amino acids that may be used are of natural or synthetic origin, in L, D, or racemic form, and comprise at least one acid function chosen for example from carboxylic acid, sulfonic acid, phosphonic acid, and phosphoric acid functions. The amino acids may be in their neutral or ionic form.

In some embodiments, the amino acids may be basic amino acids comprising an additional amine function optionally included in a ring or in a ureido function.

In some embodiments, the basic amino acids may for example be chosen from those of formula (I) below:

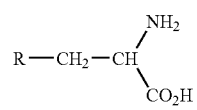

wherein R is a group chosen from:

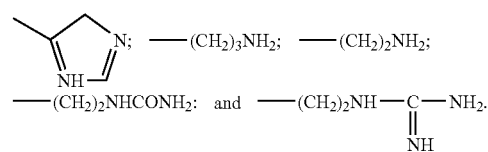

The basic amino acids of formula (I) are histidine, lysine, arginine, ornithine, and citrulline.

In some embodiments, as examples of amino acids, non-limiting mention may be made for example of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

In some embodiments, the organic amine may be chosen from basic amino acids. In certain embodiments, the amino acids may be chosen from arginine, lysine, and histidine, and mixtures thereof.

In some embodiments, the organic amine may be chosen from organic amines of a heterocyclic type. Besides histidine described herein as an amino acid, non-limiting mention may be made for example of pyridine, piperidine, imidazole, 1,2,4-triazole, tetrazole, and benzimidazole.

In some embodiments, the organic amine may be chosen from amino acid dipeptides. As examples of amino acid dipeptides that may be used, non-limiting mention may be made for example of carnosine, anserine, and baleine.

In some embodiments, the organic amine may be chosen from amines comprising a guanidine function. As amines of this type that may be used, besides arginine described herein as an amino acid, non-limiting mention may be made for example of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

In some embodiments, the organic amine may be an alkanolamine. In certain embodiments, the organic amine may be chosen from 2-amino-2-methyl-1-propanol and monoethanolamine, or mixtures thereof. In some embodiments, the organic amine may be monoethanolamine.

In some embodiments, the at least one alkaline agent may be an organic amine in salt form. "Organic amine salt" means, as used herein, organic or mineral salts of an organic amine described herein.

In some embodiments, the organic salts may be chosen from the salts of organic acids, such as citrates, lactates, glycolates, gluconates, acetates, propionates, fumarates, oxalates, and tartrates.

In some embodiments, the mineral salts may be chosen from hydrohalides (for example hydrochlorides), carbonates, hydrogen carbonates, sulfates, hydrogen phosphates, and phosphates.

"Mineral compound" means, as used herein, any compound bearing in its structure at least one element from columns 1 to 13 of the Periodic Table of the Elements other than hydrogen, provided that the at least one element does not simultaneously comprise carbon and hydrogen atoms.

In some embodiments, the mineral base may contain at least one element from columns 1 and 2 of the Periodic Table of the Elements other than hydrogen.

In some embodiments, the mineral base may have the following structure:

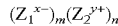

wherein $Z_2$ is a metal from columns 1 to 13, for example columns 1 or 2 of the Periodic Table of the Elements, such as sodium or potassium;

$Z_1^{x-}$ is an anion chosen from the ions $CO_3^{2-}$, $OH^-$, $HCO_3^{2-}$, $SiO_3^{2-}$, $HPO_4^{2-}$, $PO_4^{3-}$, and $B_4O_7^{2-}$, for example from the ions $CO_3^{2-}$, $OH^-$ and $SiO_3^{2-}$;

x is 1, 2, or 3;

y is 1, 2, 3, or 4;

m and n are, independently of each other, 1, 2, 3, or 4; wherein $(n)(y)=(m)(x)$.

In some embodiments, the mineral base may have the following formula $(Z_1^{x-})_m(Z_2^{y+})_n$, wherein $Z_2$ is a metal from columns 1 and 2 of the Periodic Table of the Eleme $Z_1$ is an anion chosen from the ions $CO_3^{2-}$, $OH^-$ and $SiO_3^{2-}$, x is 1, y is 1 or 2, and m and n are, independently of each other, 1 or 2 wherein $(n)(y)=(m)(x)$.

In some embodiments, as examples of mineral bases, non-limiting mention may be made of sodium bicarbonate, potassium carbonate, sodium hydroxide, potassium hydroxide, sodium metasilicate, and potassium metasilicate.

In some embodiments, ammonium salts may also be used as the at least one alkaline agent.

The ammonium salts that may be used in the composition (B) described herein are ammonium salts ($NH_4^+$).

In some embodiments, the ammonium salts that may be used in composition (B) described herein are for example chosen from the following acid salts: acetate, carbonate, bicarbonate, chloride, citrate, nitrate, nitrite, phosphate, and sulfate. In certain embodiments, the salt may be carbonate, such as ammonium carbonate.

In some embodiments, the direct emulsion (A) may comprise as the at least one alkaline agent at least one organic amine, for example at least one alkanolamine. In certain embodiments, when the direct emulsion (A) contains more than one alkaline agent including an alkanolamine and ammonium hydroxides or their salts, the amount of the at least one organic amine may for example be higher than the amount of ammonia.

In some embodiments, the at least one alkaline agent may be present in the direct emulsion (A) in an amount ranging from 0.1% to 40% by weight, for example from 0.5% to 20% by weight relative to the weight of the direct emulsion (A).

The direct emulsion (A) may comprise at least one coloring or colored species chosen from oxidation dyes and direct dyes.

In some embodiments, the oxidation dyes may be chosen from oxidation bases optionally combined with at least one coupler.

By way of example, the oxidation bases may be chosen from para-phenylenediamines, bis(phenyl)alkylenediamines, para-aminophenols, ortho-aminophenols, and heterocyclic bases, and the addition salts thereof.

Among the para-phenylenediamines, non-limiting mention may be made, for example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyDamino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and 3-hydroxy-1-(4'-aminophenyl)pyrrolidine, and the addition salts thereof with an acid.

Among the para-phenylenediamines described herein, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and 2-β-acetylaminoethyloxy-para-phenylenediamine, and the addition salts thereof with an acid, may be used.

Among the bis(phenyl)alkylenediamines, non-limiting mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and 1,8-bis(2,5-diaminophenoxy)-3,6-dioxaoctane, and the addition salts thereof.

Among the para-aminophenols, non-limiting mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, and 4-amino-2-fluorophenol, and the addition salts thereof with an acid.

Among the ortho-aminophenols, non-limiting mention may be made, for example, of 2-aminophenol, 2-amino-5-methylphenol, 2-amino-6-methylphenol, and 5-acetamido-2-aminophenol, and the addition salts thereof.

Among the heterocyclic bases, non-limiting mention may be made, for example, of pyridine derivatives, pyrimidine derivatives, and pyrazole derivatives.

Among the pyridine derivatives, non-limiting mention may be made of the derivatives described, for example, in patents GB 1 026 978 and GB 1 153 196, for instance 2,5-diaminopyridine, 2-(4-methoxyphenyl)amino-3-aminopyridine, and 3,4-diaminopyridine, and the addition salts thereof.

In some embodiments, other pyridine oxidation bases that may be used include the 3-aminopyrazolo[1,5-a]pyridine oxidation bases or addition salts thereof described, for example, in patent application FR 2 801 308. Non-limiting examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-yl-pyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)-amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, and 3-aminopyrazolo[1,5-a]pyridin-7-ol, and the addition salts thereof.

Among the pyrimidine derivatives, non-limiting mention may be made of the derivatives described, for example, in patents DE 2 359 399; JP 88-169 571; and JP 05-63124; EP 0 770 375 and patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives, non-limiting mention may be made of the derivatives described in patents DE 3 843 892 and DE 4 133 957, and patent applications WO 94/08969, WO 94/08970, FR-A-2 733 749, and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, and 3,5-diamino-4-(β-hydroxyethyl)amino-1-methylpyrazole, and the addition salts thereof. In certain embodiments, 4,5-diamino-1-(β-methoxyethyl)pyrazole may also be used.

In some embodiments, a 4,5-diaminopyrazole may be used, for example 4,5-diamino-1-(β-hydroxyethyl)pyrazole and/or a salt thereof.

Non-limiting examples of pyrazole derivatives that may also be mentioned include diamino-N,N-dihydropyrazolopyrazolones, for example the derivatives described in patent application FR-A-2 886 136, such as the following derivatives and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, and 2,3-diamino-6-hydroxy-6,7-dihydro-1H,5H-pyrazolo[1,2-a]pyrazol-1-one.

In some embodiments, 2,3-diamino-6,7-dihydro-1H,5H-pyrazolo[1,2-a]pyrazol-1-one and/or a salt thereof may for example be used.

Heterocyclic bases that may for example be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

In some embodiments, the direct emulsion (A) described herein may optionally comprise at least one coupler chosen from those conventionally used for the dyeing of keratin fibers.

Among the couplers, non-limiting mention may be made for example of meta-phenylenediamines, meta-aminophenols, meta-diphenols, naphthalene-based couplers, and heterocyclic couplers, and also the addition salts thereof.

Non-limiting mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl-indole, 2-amino-3-hydroxypyridine, 6-hydroxybenzomorpholine, 3,5-diamino-2,6-dimethoxypyridine, 1-N-(β-hydroxyethypamino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, and 6-methylpyrazolo[1,5-a]benzimidazole, the addition salts thereof with an acid, and mixtures thereof.

In general, the addition salts of the oxidation bases and couplers that may be used as disclosed herein are for example chosen from the addition salts with an acid such as the hydrochlorides, hydrobromides, sulfates, citrates, succinates, tartrates, lactates, tosylates, benzenesulfonates, phosphates, and acetates.

The at least one oxidation base may each be present in the direct emulsion (A) in an amount ranging from 0.0001% to 10% by weight relative to the total weight of the direct emulsion (A), for example from 0.005% to 5% by weight relative to the total weight of the direct emulsion (A).

The at least one coupler, if present, may each be present in the direct emulsion (A) in an amount ranging from 0.0001% to 10% by weight relative to the total weight of the direct emulsion (A), for example from 0.005% to 5% by weight relative to the total weight of the direct emulsion (A).

In some embodiments, the direct dyes may be chosen from ionic and nonionic species, for example cationic or nonionic species.

Non-limiting examples of direct dyes that may be mentioned include the following direct dyes: azo dyes; methine dyes; carbonyl dyes; azine dyes; nitro (hetero)aryl dyes; tri(hetero)arylmethane dyes; porphyrin dyes; phthalocyanin dyes, and natural direct dyes, alone or as mixtures.

In some embodiments, the azo dyes may comprise an —N=N— function, wherein the two nitrogen atoms are not simultaneously engaged in a ring. However, in certain embodiments, one of the two nitrogen atoms of the sequence —N=N— may be engaged in a ring.

In some embodiments, the dyes of the methine family may for example comprise at least one sequence chosen from —C=C— and —N=C—, wherein the two atoms are not simultaneously engaged in a ring. However, in certain embodiments, one of the nitrogen or carbon atoms of the sequences may be engaged in a ring. In some embodiments, the dyes of the methine family may be derived from dyes of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins, and hemicyanins.

As examples of dyes of the carbonyl family, non-limiting mention may be made of dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, and coumarin.

In some embodiments, as examples of dyes of the cyclic azine family, non-limiting mention may be made for example of azine, xanthene, thioxanthene, fluorindine, acridine, (di)oxazine, (di)thiazine, and pyronin.

In some embodiments, the nitro (hetero)aromatic dyes may be chosen from nitrobenzene or nitropyridine direct dyes.

In some embodiments, dyes of porphyrin or phthalocyanin type may be used including cationic or non-cationic dyes, optionally comprising at least one metal or metal ion, for instance alkali metals, alkaline-earth metals, zinc, and silicon.

Non-limiting examples of direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and for example anthraquinone, naphthoquinone or benzoquinone direct dyes; azine; xanthene; triarylmethane; indoamine; indigoid; phthalocyanin direct dyes, porphyrins, and natural direct dyes, alone or as mixtures.

These dyes may be monochromophoric dyes (i.e. comprising only one dye) or polychromophoric, for example di- or trichromophoric; the chromophores possibly being identical or different, and from the same chemical family or otherwise. It should be noted that a polychromophoric dye comprises several radicals each derived from a molecule that absorbs in the visible region between 400 and 800 nm. Furthermore, this absorbance of the dye may not require any prior oxidation thereof, or combination with any other chemical species.

In the case of polychromophoric dyes, in some embodiments, the chromophores may be connected together by means of at least one linker, which may be cationic or non-cationic.

Among the benzenic direct dyes that may be used, non-limiting mention may be made of the following compounds:
1,4-diamino-2-nitrobenzene;
1-amino-2-nitro-4-β-hydroxyethylaminobenzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis(β-hydroxyethyDamino-3-nitrobenzene;
1-β-hydroxyethylamino-2-nitrobenzene; and
1-hydroxy-4-β-hydroxyethylamino-3-nitrobenzene.

Among the azo, azomethine, methine and tetraazapentamethine direct dyes that may be used, non-limiting mention may be made of the cationic dyes described in patent applications WO 95/15144, WO 95/01772, EP 714 954, FR 2 189 006, FR 2 285 851, FR 2 140 205, EP 1 378 544, and EP 1 674 073.

Among the cationic dyes, non-limiting mention may also be made of the following compounds:

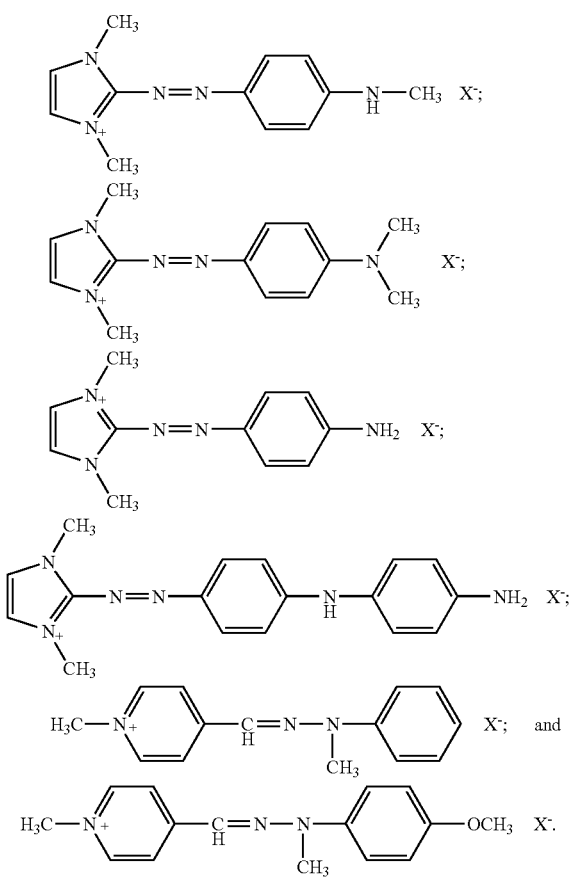

Among the azo direct dyes, non-limiting mention may be made of the following dyes, described in the Colour Index International, 3rd edition:
Disperse Red 17;
Basic Red 22;
Basic Red 76;
Basic Yellow 57;
Basic Brown 16;
Basic Brown 17; and
Disperse Black 9.

Non-limiting mention may also be made of 1-(4'-aminodiphenylazo)-2-methyl-4-bis(β-hydroxyethyl)aminobenzene.

Among the quinone direct dyes, non-limiting mention may be made of the following dyes:
Disperse Red 15;
Solvent Violet 13;
Disperse Violet 1;
Disperse Violet 4;
Disperse Blue 1;
Disperse Violet 8;
Disperse Blue 3;
Disperse Red 11;
Disperse Blue 7;
Basic Blue 22;
Disperse Violet 15; and
Basic Blue 99;
and also of the following dyes:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-aminoethylaminoanthraquinone; and
1,4-bis(β,γ-dihydroxypropylamino)anthraquinone.

Among the azine dyes, non-limiting mention may be made of the following dyes:
Basic Blue 17 and
Basic Red 2.

Among the triarylmethane dyes, non-limiting mention may be made of the following dyes:
Basic Green 1;
Basic Violet 3;
Basic Violet 14;
Basic Blue 7; and
Basic Blue 26.

Among the indoamine dyes, non-limiting mention may be made of the following compounds:
2β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N-(2'-chloro-4'-hydroxy)phenylacetylamino-6-methoxy-1,4-benzoquinone imine;
3-N-(3'-chloro-4'-methylamino)phenyluredo-6-methyl-1,4-benzoquinone imine; and
3-[4'-N-(ethyl,carbamylmethyl)amino]phenylureido-6-methyl-1,4-benzoquinone imine.

Among the dyes of tetraazapentamethine, non-limiting mention may be made of the following dyes given in the table below, as described herein:

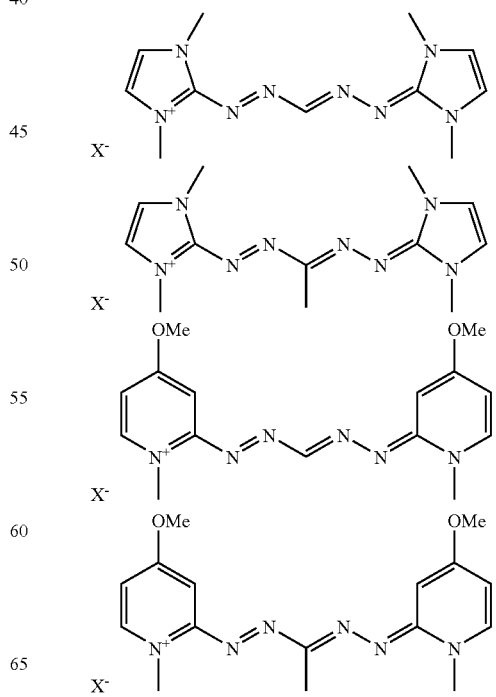

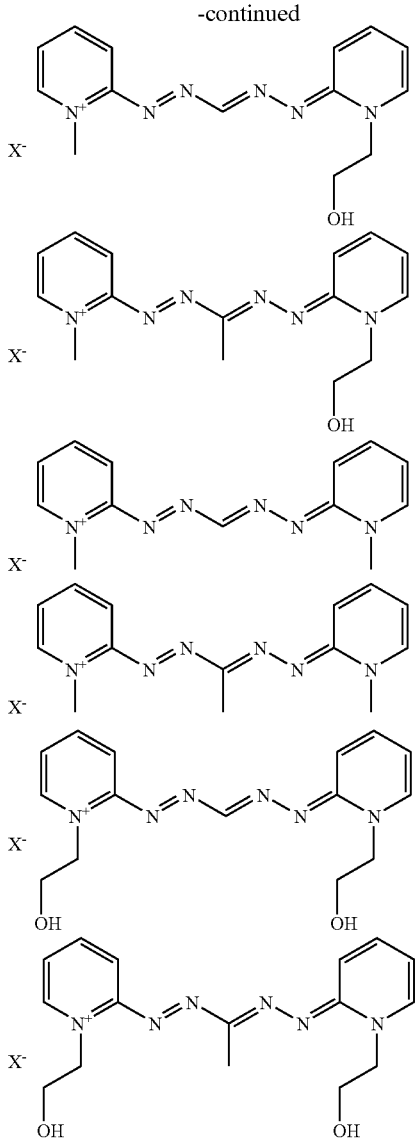

wherein X⁻ is an anion for example chosen from chloride, iodide, methyl sulfate, ethyl sulfate, acetate and, perchlorate.

As examples of polychromophoric dyes, non-limiting mention may be made to the dyes described in EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

In some embodiments, non-limiting mention may be made of the cationic direct dyes described in patent applications: EP 1 006 153, which describes dyes comprising two chromophores of anthraquinone type connected via a linker of cationic type; EP 1 433 472, EP 1 433 474, EP 1 433 471 and EP 1 433 473, which describe identical or different dichromophoric dyes, connected via a cationic or non-cationic linker, and EP 6 291 333, which describes dyes comprising three chromophores, one of them being an anthraquinone chromophore, to which are attached two chromophores of azo or diazacarbocyanin type or an isomer thereof.

Among the natural direct dyes, non-limiting mention may be made of lawsone, juglone, alizarin, purpurin, carminic acid, kermesic acid, purpurogallin, protocatechaldehyde, indigo, isatin, curcumin, spinulosin, apigenidin, and orceins. In some embodiments, extracts or decoctions containing the natural dyes and especially henna-based poultices or extracts may be used.

When they are present, the at least one direct dye may be present in the direct emulsion (A) in an amount ranging from 0.0001% to 10% by weight, for example from 0.005% to 5% by weight relative to the total weight of the direct emulsion (A).

In some embodiments, the direct emulsion (A) may comprise at least one other type of dye. In certain embodiments, the direct emulsion (A) may optionally be derived from the mixing of two dye compositions, one comprising the oxidation dye and the other comprising the direct dye.

The direct emulsion (A) may also contain various adjuvants conventionally used in compositions for lightening the hair, such as anionic, cationic, nonionic, amphoteric, or zwitterionic polymers or mixtures thereof; mineral thickeners; and for example fillers such as clays or talc; organic thickeners, for instance with anionic, cationic, nonionic, and amphoteric polymeric associative thickeners; antioxidants; penetrants; sequestrants; fragrances; dispersants; film-forming agents; preserving agents; and opacifiers.

The direct emulsion (A) may optionally comprise at least one organic solvent. Non-limiting examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, glycerol, diethylene glycol monomethyl ether, and monoethyl ether, and also aromatic alcohols, for instance benzyl alcohol or phenoxyethanol, and mixtures thereof.

The process described herein may be performed with a composition (B) comprising at least one oxidizing agent.

In some embodiments, the at least one oxidizing agent is chosen from hydrogen peroxide, urea peroxide, alkali metal bromates or ferricyanides, peroxygenated salts, for instance persulfates, perborates, peracids and precursors thereof, and percarbonates of alkali metals or alkaline-earth metals.

In some embodiments, the at least one oxidizing agent may be formed from hydrogen peroxide, for example as an aqueous solution (aqueous hydrogen peroxide solution), whose titer may range, for example, from 1 to 40 volumes (i.e. 0.3% to 12% $H_2O_2$) and for instance from 5 to 40 volumes (i.e. 1.5% to 12% $H_2O_2$).

Depending on the desired degree of lightening, the at least one oxidizing agent may also comprise an oxidizing agent for example chosen from peroxygenated salts.

In some embodiments, composition (B) may be generally an aqueous composition. "Aqueous composition" means, as used herein, a composition comprising more than 5% by weight of water, for example more than 10% by weight of water, and for instance more than 20% by weight of water.

In some embodiments, the composition (B) may also comprise at least one organic solvent described herein. In certain embodiments, it may also comprise at least one acidifying agent.

Among the acidifying agents, non-limiting examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

In some embodiments, the pH of composition (B) may be less than 7.

In some embodiments, the composition (B) may be in various forms, for instance a solution, an emulsion, or a gel.

In some embodiments, the process described herein may be performed by applying the direct emulsion (A) and composition (B) successively and without intermediate rinsing.

In some embodiments, a composition obtained by extemporaneous mixing, at the time of use, of the direct emulsion (A) and of composition (B) may be applied to wet or dry keratin materials. In some embodiments, the weight ratio of the amount of the direct emulsion (A) to composition (B) ranges in value from 0.1 to 10, for example from 0.2 to 2 and for instance from 0.3 to 1.

In some embodiments, the direct emulsion (A) and the composition (B) may be mixed prior to applying the resultant composition to keratin fibers.

In some embodiments, the mixture present on the keratin materials (resulting either from the extemporaneous mixing of the direct emulsion (A) and composition (B) or from their partial or total successive application) may be left in place for a time period ranging from 1 minute to 1 hour and for example from 5 minutes to 30 minutes.

The temperature during the process described herein may conventionally range from room temperature (ranging from 15 to 25° C.) to 80° C. and for example from room temperature to 60° C.

In some embodiments, after the treatment, the keratin materials may be optionally rinsed with water, optionally subjected to washing followed by rinsing with water, and may then be dried or left to dry.

In some embodiments, the keratin materials may be keratin fibers such as bodily hair, eyelashes, or head hair.

In some embodiments, the dyeing composition obtained after the mixing of the direct emulsion (A) described herein and the composition (B) described herein comprising at the least one oxidative agent, may contain at least one fatty substance in an amount greater than 20% by weight relative to the total weight of the dyeing composition, for example greater than 25% by weight, and for instance greater than 30% by weight.

Also provided is a multi-compartment device comprising, in a first compartment, a direct emulsion (A) described herein, and, in a second compartment, an aqueous composition (B) described herein comprising at least one oxidizing agent, described herein.

The following examples illustrate the disclosure but are not in any way limiting.

EXAMPLES

The direct emulsion A1 below was prepared according to a phase inversion temperature process (PIT process).

Manufacturing Process:

Phase A was heated on a water bath with Rayneri blending (400 rpm). A fluid white emulsion that became translucent at about 68° C. (passing through a microemulsion phase) and thickened above this temperature was obtained.

Once the emulsion had thickened, the water bath was removed, and the emulsion was allowed to cool with continued stirring.

At about 50° C., the poloxamer was introduced.

At room temperature, the ethanol, the monoethanolamine, the potassium bicarbonate, the base and the coupler predispersed in 4.302 g of water were introduced, and the water lost on evaporation (<5%) was readjusted.

A translucent gelled emulsion with droplet sizes<1 μm (viscosity=8 DU M4, droplet size<1 μm, pH 11.3) was thus obtained.

| Emulsion A1 | | |
|---|---|---|
| Phase | INCI Name | g % |
| A | Beheneth-10 | 6.00 |
| | Sorbitol | 5.00 |
| | Liquid petroleum jelly | 60.25 |
| | Water | 10.00 |
| B | Ethanol | 2.00 |
| | Poloxamer 184 | 5.00 |
| | Potassium bicarbonate | 1.75 |
| | Water | 4.302 |
| | Monoethanolamine | 5.00 |
| | p-Phenylenediamine | 0.216 |
| | 2,4-Diaminophenoxyethanol dihydrochloride | 0.482 |

At the time of use, 1 weight of the direct emulsion A1 was mixed with 1.5 weights of an oxidizing aqueous composition (B1) comprising a dispersion of fatty alcohols (8%) in water and aqueous 6% hydrogen peroxide solution: Platinum 20V.

The mixture was then applied to a lock of natural 90% grey hair (tone height=4). The bath ratio "mixture/lock" had a value of, respectively, 10/1 (g/g). The leave-on time period was 30 minutes at 27° C. After this time, the locks were rinsed and then washed with Elsève multivitamin shampoo.

A strong blue coloration was obtained, without odor.

What is claimed is:

1. A process for dyeing keratin materials, comprising: applying to said keratin materials a dyeing composition comprising,
a direct emulsion (A) comprising at least one fatty substance other than fatty acids present in an amount greater than 25% by weight; at least one surfactant; at least one alkaline agent; at least one colored or coloring entity chosen from direct dyes and oxidation dyes; and water in an amount less than or equal to 50% by weight relative to the total weight of the direct emulsion (A); and
a composition (B) comprising at least one oxidizing agent,
wherein the at least one fatty substance other than fatty acids is chosen from compounds that are liquid at room temperature and at atmospheric pressure.

2. The process according to claim 1, wherein the at least one fatty substance other than fatty acids is present in an amount greater than 50% by weight of the direct emulsion (A).

3. The process according to claim 1, wherein the water is present in the direct emulsion (A) in an amount greater than 10% by weight of the direct emulsion (A).

4. The process according to claim 3, wherein the water is present in the direct emulsion (A) in an amount ranging from 10% to 50% by weight.

5. The process according to claim 1, wherein the at least one fatty substance other than fatty acids is chosen from alkanes of 6 to 16 carbon atoms, fatty alcohols, fatty acid esters, fatty alcohol esters, mineral oils of more than 16 carbon atoms, non-silicone plant, animal oils, synthetic oils, silicones and non-silicone waxes.

6. The process according to claim 1, wherein the at least one fatty substance other than fatty acids is present in an amount ranging from 25% to 80% by weight relative to the weight of the direct emulsion (A).

7. The process according to claim 1, wherein the direct emulsion (A) further comprises at least one nonionic surfactant.

8. The process according to claim 7, wherein the at least one nonionic surfactant is chosen from monooxyalkylenated, polyoxyalkylenated, monoglycerolated and polyglycerolated nonionic surfactants.

9. The process according to claim 1, wherein the at least one alkaline agent is chosen from organic amines, mineral bases, organic amine salts, and ammonium salts.

10. The process according to claim 9, wherein the at least one organic amine is chosen from alkanolamines and basic amino acids.

11. The process according to claim 9, wherein the at least one alkanolamine is chosen from 2-amino-2-methyl-1-propanol and monoethanolamine.

12. The process according to claim 9, wherein the at least one organic amine is chosen from arginine, histidine, and lysine.

13. The process according to claim 1, wherein the at least one oxidation dye is chosen from para-phenylenediamines, bis(phenyl)alkylenediamines, para-aminophenols, ortho-aminophenols, heterocyclic bases and addition salts thereof, meta-phenylenediamines, meta-aminophenols, meta-diphenols, naphthalene-based couplers and heterocyclic couplers, and addition salts thereof.

14. The process according to claim 1, wherein the at least one direct dye is chosen from azo dyes, methine dyes, carbonyl dyes, azine dyes, nitro (hetero)aryl dyes, tri(hetero)arylmethane dyes, porphyrin dyes, phthalocyanin dyes, and natural direct dyes.

15. The process according to claim 1, wherein the composition (B) comprises at least one oxidizing agent chosen from hydrogen peroxide, urea peroxide, alkali metal bromates and ferricyanides, and peroxygenated salts.

16. The process according to claim 15, wherein the at least one oxidizing agent is chosen from peroxygenated salts chosen from perborates, peracids and precursors thereof, and percarbonates of alkali metals and alkaline-earth metals.

17. The process according to claim 15, wherein the at least one oxidizing agent is hydrogen peroxide.

18. The process according to claim 1, wherein the composition (B) comprises more than 5% by weight of water.

19. The process according to claim 18, wherein the composition (B) comprises more than 20% by weight of water.

20. The process according to claim 1, wherein the direct emulsion (A) and the composition (B) are mixed prior to applying the resultant composition to keratin fibers.

21. The process according to claim 1, wherein the direct emulsion (A) and composition (B) are applied to the keratin fibers successively and without intermediate rinsing.

22. A multi-compartment device comprising, in a first compartment, a direct emulsion (A) comprising at least one fatty substance other than fatty acids present in an amount greater than 25% by weight; at least one surfactant; at least one alkaline agent; at least one colored or coloring entity chosen from direct dyes and oxidation dyes; and water in an amount less than or equal to 50% by weight relative to the total weight of the direct emulsion (A); and, in another compartment, a composition (B) comprising at least one oxidizing agent,
wherein the at least one fatty substance other than fatty acids is chosen from compounds that are liquid at room temperature and at atmospheric pressure.

* * * * *